US009277923B2

(12) United States Patent
Rangi (10) Patent No.: US 9,277,923 B2
(45) Date of Patent: Mar. 8, 2016

(54) BALLOON ASSISTED OCCLUSION OF ANEURYSMS

(75) Inventor: Permjit Rangi, Romford (GB)

(73) Assignee: BARKING HAVERING & REDBRIDGE HOSPITALS NHS TRUST, Rumford (GB)

( * ) Notice: Subject to any disclaimer, the term of this patent is extended or adjusted under 35 U.S.C. 154(b) by 474 days.

(21) Appl. No.: 13/262,341

(22) PCT Filed: Mar. 30, 2010

(86) PCT No.: PCT/GB2010/000619
§ 371 (c)(1),
(2), (4) Date: Jan. 10, 2012

(87) PCT Pub. No.: WO2010/112838
PCT Pub. Date: Oct. 7, 2010

(65) Prior Publication Data
US 2012/0116352 A1    May 10, 2012

(30) Foreign Application Priority Data
Mar. 31, 2009    (GB) .................................. 0905556.7

(51) Int. Cl.
*A61M 29/00*    (2006.01)
*A61B 17/12*    (2006.01)
*A61M 25/10*    (2013.01)
(Continued)

(52) U.S. Cl.
CPC ..... *A61B 17/12022* (2013.01); *A61B 17/12045* (2013.01); *A61B 17/12113* (2013.01); *A61B 17/12136* (2013.01); *A61M 25/1011* (2013.01); *A61B 2017/00557* (2013.01); *A61B 2017/1205* (2013.01); *A61B 2017/22054* (2013.01); *A61B 2017/22065* (2013.01); *A61B 2017/22067* (2013.01); *A61B 2017/22068* (2013.01); *A61B 2017/22069* (2013.01); *A61M 2025/1045* (2013.01)

(58) Field of Classification Search
USPC .......... 606/191, 194, 198, 200; 604/508, 509, 604/510
See application file for complete search history.

(56) References Cited

U.S. PATENT DOCUMENTS

| | | | |
|---|---|---|---|
| 5,405,322 A | | 4/1995 | Lennox et al. |
| 5,720,735 A | * | 2/1998 | Dorros .......................... 604/284 |

(Continued)

FOREIGN PATENT DOCUMENTS

| | | |
|---|---|---|
| EP | 1 266 629 A1 | 12/2002 |
| WO | 98/26832 A1 | 6/1998 |

(Continued)

OTHER PUBLICATIONS

International Search Report mailed May 17, 2010 for Application No. PCT/GB2010/000619 (4 Pages).
(Continued)

*Primary Examiner* — Tuan V Nguyen
(74) *Attorney, Agent, or Firm* — Norton Rose Fulbright US LLP (57) ABSTRACT

A catheter and related methods for percutaneous treatment of an aneurysm. The present catheters include an outlet for deploying an occluding agent; and a deflector for deflecting the occluding agent. A second deflector may be provided to cooperate with the first deflector. One or both of the deflectors may each include an inflatable balloon. The occluding agent may include a length of wire.

13 Claims, 7 Drawing Sheets

(51) Int. Cl.
*A61B 17/00* (2006.01)
*A61B 17/22* (2006.01)

(56) References Cited

U.S. PATENT DOCUMENTS

| | | | |
|---|---|---|---|
| 5,916,194 A * | 6/1999 | Jacobsen et al. | 604/96.01 |
| 6,048,333 A | 4/2000 | Lennox et al. | |
| 6,096,021 A | 8/2000 | Helm et al. | |
| 6,196,230 B1 | 3/2001 | Hall et al. | 128/898 |
| 6,251,093 B1 * | 6/2001 | Valley et al. | 604/97.03 |
| 6,261,304 B1 | 7/2001 | Hall et al. | 606/194 |
| 6,387,119 B2 | 5/2002 | Wolf et al. | 606/108 |
| 6,409,751 B1 | 6/2002 | Hall et al. | 623/1.11 |
| 6,527,790 B2 * | 3/2003 | Chien et al. | 606/194 |
| 6,605,074 B2 | 8/2003 | Zadno-Azizi et al. | |
| 6,694,983 B2 | 2/2004 | Wolf et al. | 128/898 |
| 7,695,488 B2 | 4/2010 | Berenstein et al. | 606/194 |
| 7,959,667 B2 * | 6/2011 | Ta et al. | 623/1.35 |
| 8,292,900 B2 * | 10/2012 | Meyer et al. | 606/108 |
| 2003/0060756 A1 | 3/2003 | Hayman et al. | |
| 2004/0068289 A1 | 4/2004 | Cheng et al. | |
| 2004/0102805 A1 * | 5/2004 | Cheng et al. | 606/191 |
| 2004/0186507 A1 | 9/2004 | Hall et al. | 606/194 |
| 2005/0004660 A1 | 1/2005 | Rosenbluth et al. | |
| 2005/0015108 A1 | 1/2005 | Williams et al. | |
| 2005/0060027 A1 * | 3/2005 | Khenansho et al. | 623/1.35 |
| 2006/0004329 A1 | 1/2006 | Hebert et al. | |
| 2006/0036315 A1 * | 2/2006 | Yadin et al. | 623/1.35 |
| 2006/0106448 A1 | 5/2006 | Shaked | |
| 2007/0219578 A1 * | 9/2007 | Solar et al. | 606/200 |
| 2010/0168781 A1 | 7/2010 | Berenstein et al. | 606/191 |

FOREIGN PATENT DOCUMENTS

| | | |
|---|---|---|
| WO | 02/45597 A2 | 6/2002 |
| WO | 03/020357 A1 | 3/2003 |
| WO | 2007/105217 A2 | 9/2007 |
| WO | 2009/050478 A1 | 4/2009 |

OTHER PUBLICATIONS

United Kingdom Search Report issued Jun. 5, 2009 for Application No. GB0905556.7 (2 Pages).

* cited by examiner

BALLOON ASSISTED OCCLUSION OF ANEURYSMS

BACKGROUND OF THE INVENTION

The present invention relates to the percutaneous treatment of aneurysms, and in particular apparatus and methods for balloon assisted occlusion of cerebral aneurysms.

Aneurysms of the cerebral arteries are areas of blood vessel which have been weakened through disease or injury and have subsequently expanded due to the pressure of blood flow.

Cerebral aneurysms are particularly dangerous as thrombus (blood clot) formation can occur within the aneurismal sac, greatly increasing the risk of emboli formation and stroke. In addition, as the vessel is weakened at the aneurysm site, blood vessel rupture is more likely. This condition, if left untreated, quickly results in death.

Traditional treatment of cerebral aneurysm at risk of rupture has been a craniotomy (drilling through the skull) and occlusion using a cerebral clip. This operation carries significant risk and complexity due to its invasive nature. It is also only indicated for a narrow selection of patients due to that risk and because some parts of the cerebral vasculature are simply not accessible through the skull without having to damage the brain.

Cerebral aneurysms fall into two main anatomical variants, which are illustrated in FIGS. 1a to 2b: 1) "saccular aneurysms" 100 (see FIGS. 1a and 1b), which as their name suggests are round sack-like distensions 100 with a narrow opening 102 into the native vessel 104; and 2) "fusiform aneurysms" 200 (see FIGS. 2a and 2b), which are concentric distensions 200 of the blood vessel 104 with less well-defined edges than a saccular aneurysm 100.

Figure 1A:
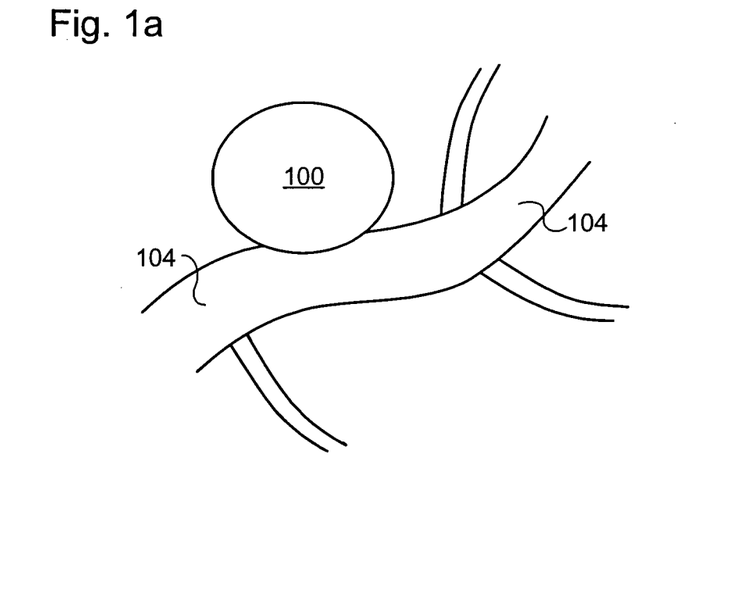
FIG. 1a shows a saccular aneurysm in 3-d.
Figure 1B:
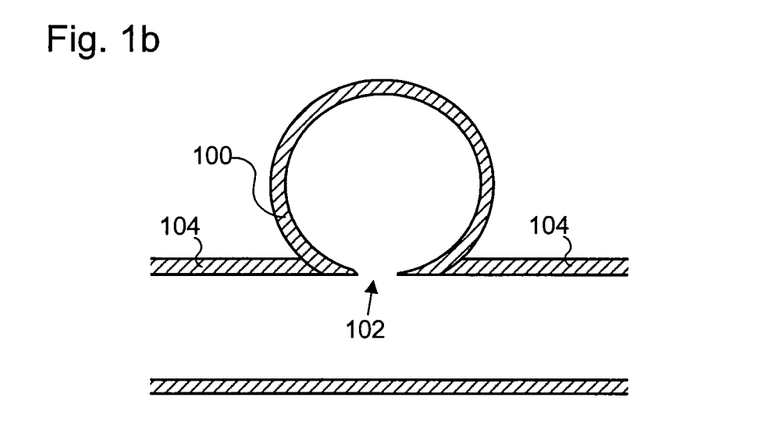
FIG. 1b shows a saccular aneurysm in cross section.
Figure 2A:
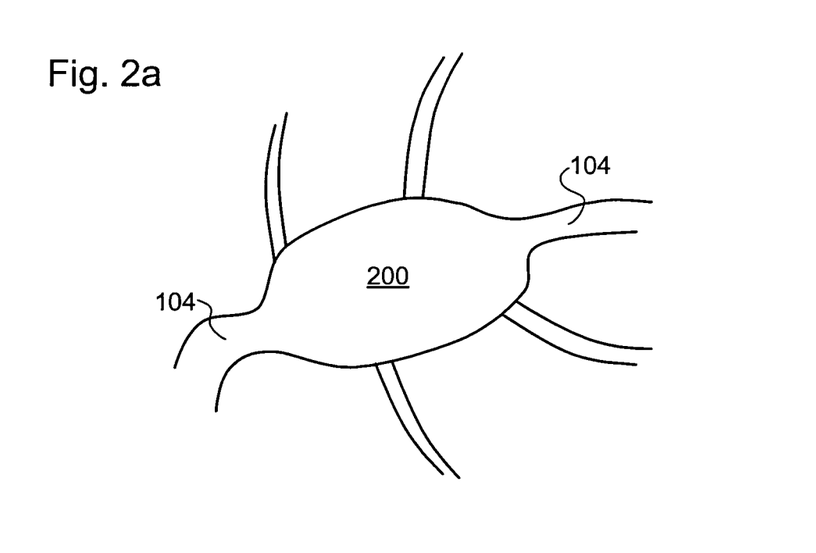
FIG. 2a shows a fusiform aneurysm in 3-d.
Figure 2B:
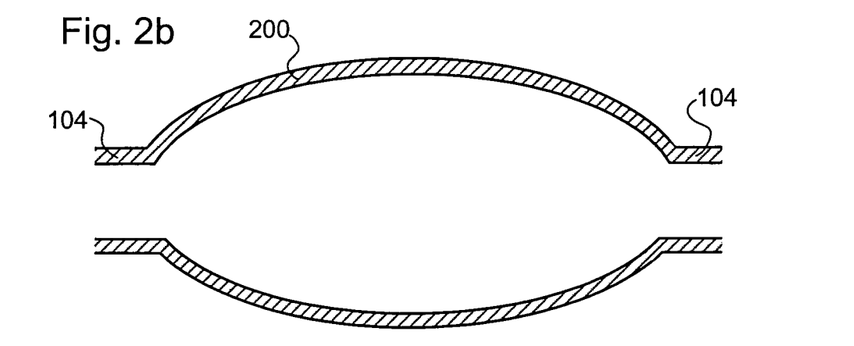
FIG. 2b shows a fusiform aneurysm in cross section.
Figure 3A:
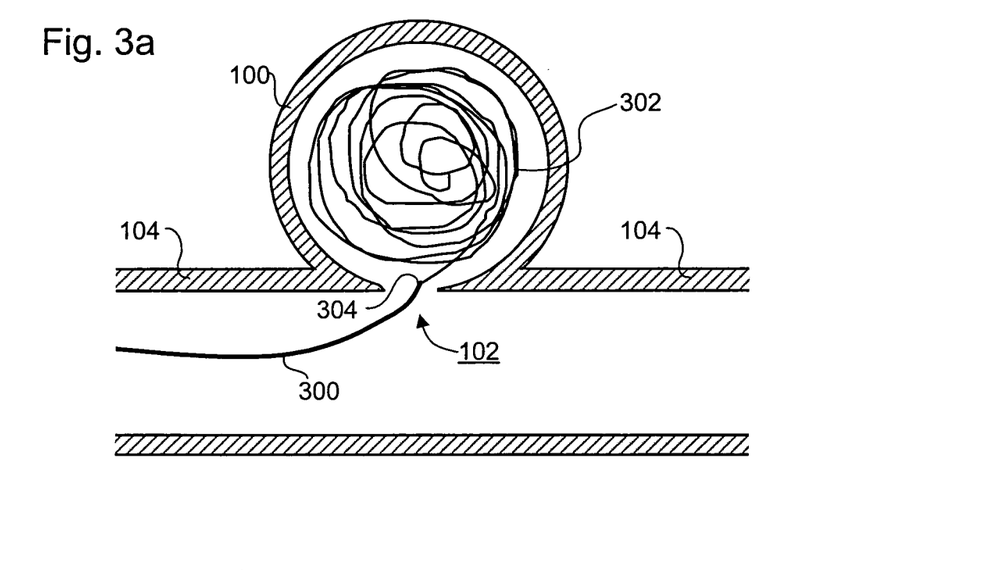
FIG. 3a shows a saccular aneurysm being treated with a simple coil embolisation.

In recent years, percutaneous techniques have arisen to treat cerebral aneurysms using wire coils to artificially embolise the distended tissue. FIG. 3a illustrates application of this technique to a saccular aneurysm 100. A catheter 300 is fed up to the aneurysm mouth 102 where a platinum wire 302 is pushed out of the catheter tip 304, into the aneurismal sac 100. This wire 302 then coils into the sac 100, progressively occluding the aneurysm 100. When enough wire 302 is implanted, the clinician can simply disconnect the wire 302, which should stay in place.

This method is well established and has been in use since 1991. However, it is generally only applicable for narrow necked, saccular aneurysms 100 as these shapes lend themselves well to the wire 302 coiling round into a ball.

For wider necked aneurysms 320 (see FIG. 3b), i.e. those which are less saccular and more fusiform, this process may not be possible, as the wire 302 will tend to exit the aneurysm mouth into the native vessel 104. This scenario should be avoided as wire 302 coils in the blood stream may pose a thrombus risk.

Figure 3B:
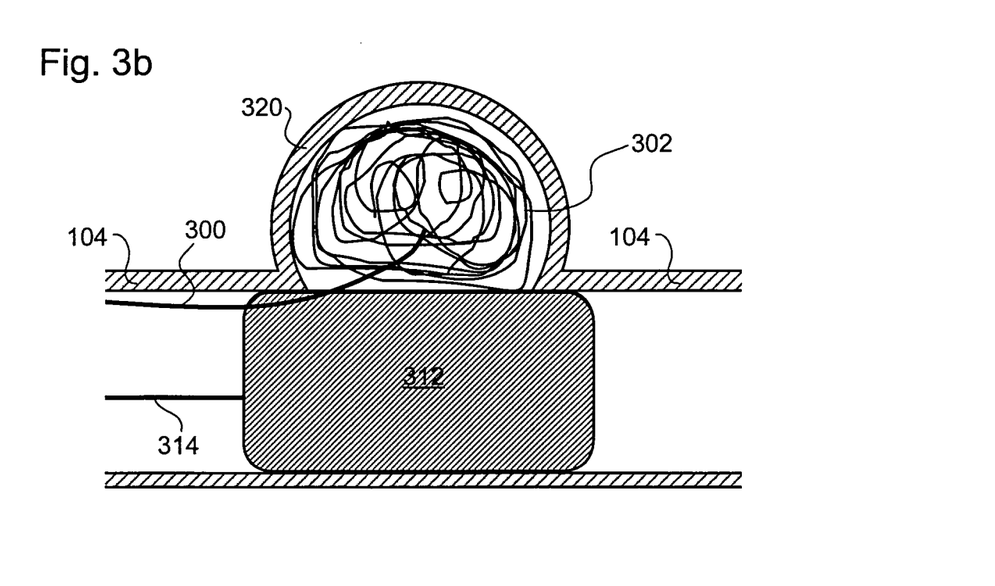
FIG. 3b shows a wider necked aneurysm being treated with the same coil dispensing type catheter as in FIG. 3a, with an additional compliant balloon catheter.

FIG. 3b illustrates one approach that clinicians have used to avoid this. A compliant balloon 312 is positioned at the site of interest via a second catheter 314 and used to force the wire 302 round and back into the aneurismal sac 320. On inflation, the balloon 312 conforms to the local vessel anatomy forming a barrier to the coiling wire 302. Such balloons 312 can only be inflated for a maximum of 2 minutes at a time because, when inflated, they occlude blood flow through the vessel 104.

This prior art procedure requires the coil delivery catheter 300 and at least one balloon delivery system to occlude the aneurysm. As separate units, these devices cause significant crowding in an already small vessel 104 and, due to the high compliance of the deployed balloon, there is little scope for manoeuvring to re-adjust the delivery catheter 300 if multiple balloons were to be used.

An object of the present invention is to overcome at least some of the problems associated with the prior art.

BRIEF SUMMARY OF THE INVENTION

According to an aspect of the invention, there is provided a catheter for percutaneous treatment of an aneurysm, comprising: an outlet for deploying an occluding agent; and a first deflector for deflecting said occluding agent.

Having a single catheter with its own deflector enables an occluding agent to be delivered reliably into an aneurysm with a minimum of crowding in the region of treatment. In addition, all the equipment required for the procedure is contained on the one device.

Optionally, the occluding agent comprises a length of wire to be coiled into a ball in the aneurysm. The wire may be formed from a suitably inert metal such as platinum. The first or second deflector may comprise an inflatable balloon and/or be configured to deflect the occluding agent after it has left the outlet.

Optionally, the catheter may comprise a second deflector, which may also comprise an inflatable balloon. Either or both of the first and second deflectors may be configured to shift the position and/or orientation of the outlet. The two deflectors thus provide enhanced control of how the occluding agent is deployed, thus improving the reliability and safety of treatment.

The first and second deflectors may be configured to be actuatable selectively and/or to a variable extent so as cooperatively to adjust the direction of deployment of the occluding agent and/or the position and/or orientation of the outlet. Sequential and independent balloon inflation allows accurate positioning of the coil catheter for precise coil placement.

According to an alternative aspect of the invention, there is provided a method of treating an aneurysm, comprising: percutaneously inserting a catheter according to any one of the preceding claims so that a distal end thereof is brought into the region of the aneurysm; using said outlet to deploy an occluding agent; and using said first deflector to deflect said deployed occluding agent into said aneurysm.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 4A:
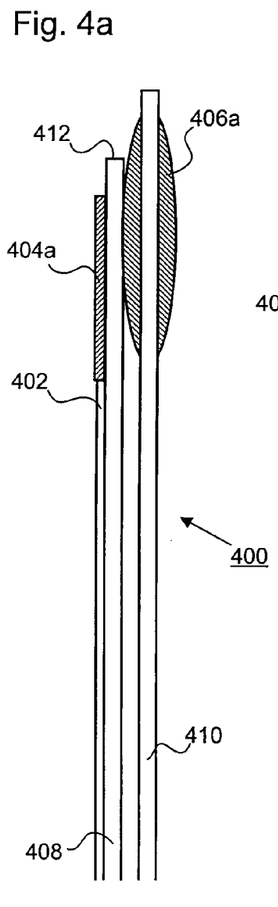
FIG. 4a shows a combination catheter according to an embodiment of the invention, in an un-actuated state.
Figures 4B, 4C:
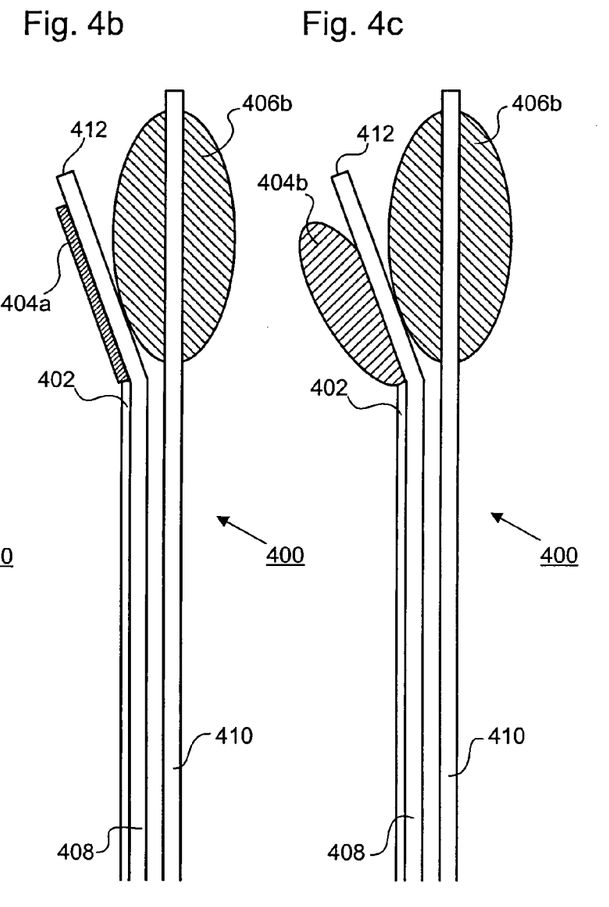
FIG. 4b shows the combination catheter of FIG. 4a with a primary balloon inflated so as to deflect a coil outlet.
FIG. 4c shows the combination catheter of FIG. 4b after actuation of a secondary balloon.

FIGS. 4a to 4c depict a catheter 400 according to an embodiment of the invention in three different states of actuation.

The catheter 400 comprises a primary stem 410, a secondary stem 408 and a tertiary stem 402. At a distal end of the catheter 400, the primary stem 410 comprises a first controllably expandable balloon 406a/406b, the secondary stem 408 comprises an outlet 412 for an occluding agent, and the tertiary stem 402 comprises a second controllably expandable balloon 404a/404b.

FIG. 4a depicts the catheter 400 before actuation; the first and second balloons 406a and 406b are both deflated and the outlet 412 is directed parallel to a longitudinal axis of the catheter 400 at the distal end (i.e. the end that will be pushed inside the vessel 104 to the treatment site).

FIG. 4b shows the catheter 400 after actuation of the first balloon to an inflated state 406a. At the distal end of the catheter 400, the secondary stem 408 is rotated anticlockwise so that the outlet orientation and position is changed. Occluding agent will thus be output in a different direction and from a different starting location in the configuration of FIG. 4b in comparison with the situation in FIG. 4a.

FIG. 4c shows the catheter 400 after actuation of the second balloon to an inflated state 404b. Inflation of the second balloon can be used to adjust the position and/or orientation of the outlet 412 further by pressing against the vessel wall 104 (and thereby pushing the distal end of the catheter 400 further away from the region of contact between the inflated second balloon 404b and the vessel wall 104). An example of this function is shown in FIG. 4d.

Figure 4D:
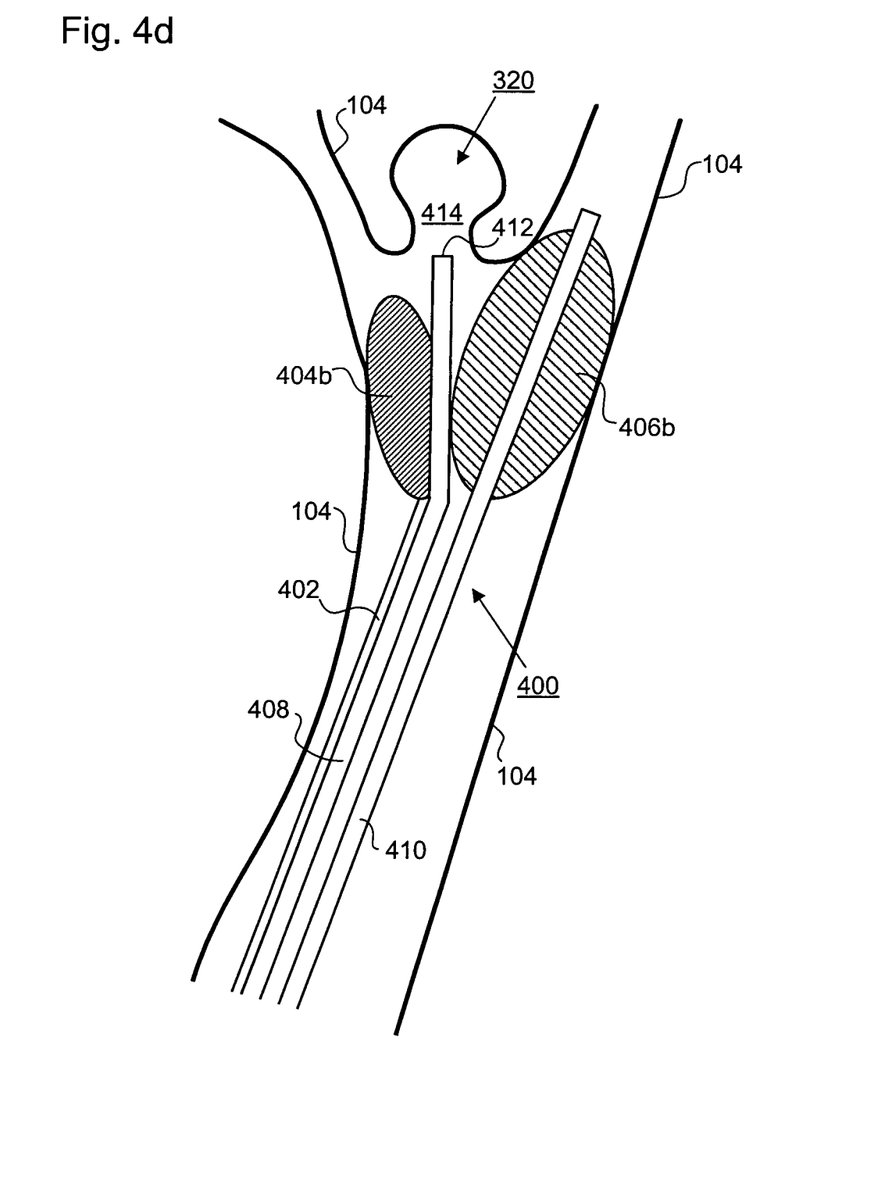
FIG. 4d illustrates the fully actuated device of FIG. 4c in situ.

FIG. 4d shows the fully actuated catheter 400 in situ in the body to be treated. The first and second balloons have both been actuated to inflated states 406b and 404b so as to guide the outlet 412 into a position opposite to the neck 414 of the aneurysm 320 and oriented so that an occluding agent will enter the aneurysm reliably and with a minimal risk of leakage of the occluding agent into the portion of the vessels 104 outside of the aneurismal sac.

In the examples shown, the first balloon expands substantially symmetrically in two directions either side of the longitudinal axis of the primary stem 410 (i.e. two lobes are present in an axial sectional view). Alternatively, the first balloon 406a/406b may expand coaxially so as to extend radially outwards in all directions (to the same or different relative extents). Further alternatively, the first balloon 406a/406b may expand radially so as to form a single sectional lobe or three or more sectional lobes. The first balloon may be compliant and conform to the shape of the portion of the vessel 104 within which it is located, for example so as to substantially block this portion of the vessel 104.

The catheter 400 may be arranged so that inflation of the first balloon 406a/406b simultaneously causes: 1) the catheter 400 to be pushed away from a part of the wall of the vessel 104 with which the inflated first balloon 406b comes into contact; and 2) the secondary stem 408 to deflect to as to adjust the orientation of the outlet 412.

In the examples shown, the second balloon 404a/404b expands predominantly in a single sectional lobe (to the left in FIG. 4d), so as to push the catheter 400 away from a region of contact between the inflated second balloon 404b and the vessel 104 (i.e. to the right in FIG. 4d). However, other arrangements are possible. For example, the multiple lobe arrangements discussed above in respect of the inflated first balloon 406b could also be used for the inflated second balloon 404b.

In the example shown, the primary, secondary and tertiary stems are parallel, but other arrangements are possible. Arrangements having fewer than three stems can also be envisaged. For example, the functionality associated with the three stems may be incorporated into a single stem or two stems.

In the examples shown, the second balloon 404a/404b is positioned near a distal end of the catheter 400, in close proximity to the first balloon 406a/406b. However, the function of controllably displacing the catheter 400 by inflating the second balloon 404a/404b could be achieved via a balloon located further away from the distal end of the catheter 400 (i.e. further downwards in FIGS. 4a to 4d).

Deflection mechanisms other than balloons may also be provided, for deflecting the position of the distal end of the catheter 400, for deflecting the orientation of the outlet 412 relative to the main longitudinal axis of the catheter 400 (near the distal end, for example relative to the stem 410 near the distal end), and/or for deflecting a direction of deployment of the occluding agent after it has left the outlet 412 (or of a portion of the occluding agent that has left the outlet 412).

In the particular example shown in the FIGS. 4a to 4d, two balloons are used to deflect (control) the position and/or orientation of the occluding agent outlet 412. Neither of the two balloons in this example are arranged to influence the direction of deployment of the occluding agent after it has left the outlet 412 (or of a portion of the occluding agent that has left the outlet—for example, a length of deployed wire). However, one or both of the balloons may be arranged to do this. For example, the first balloon may be configured to provide this functionality in addition to influencing the position and/or orientation of the outlet 412.

Figure 5:
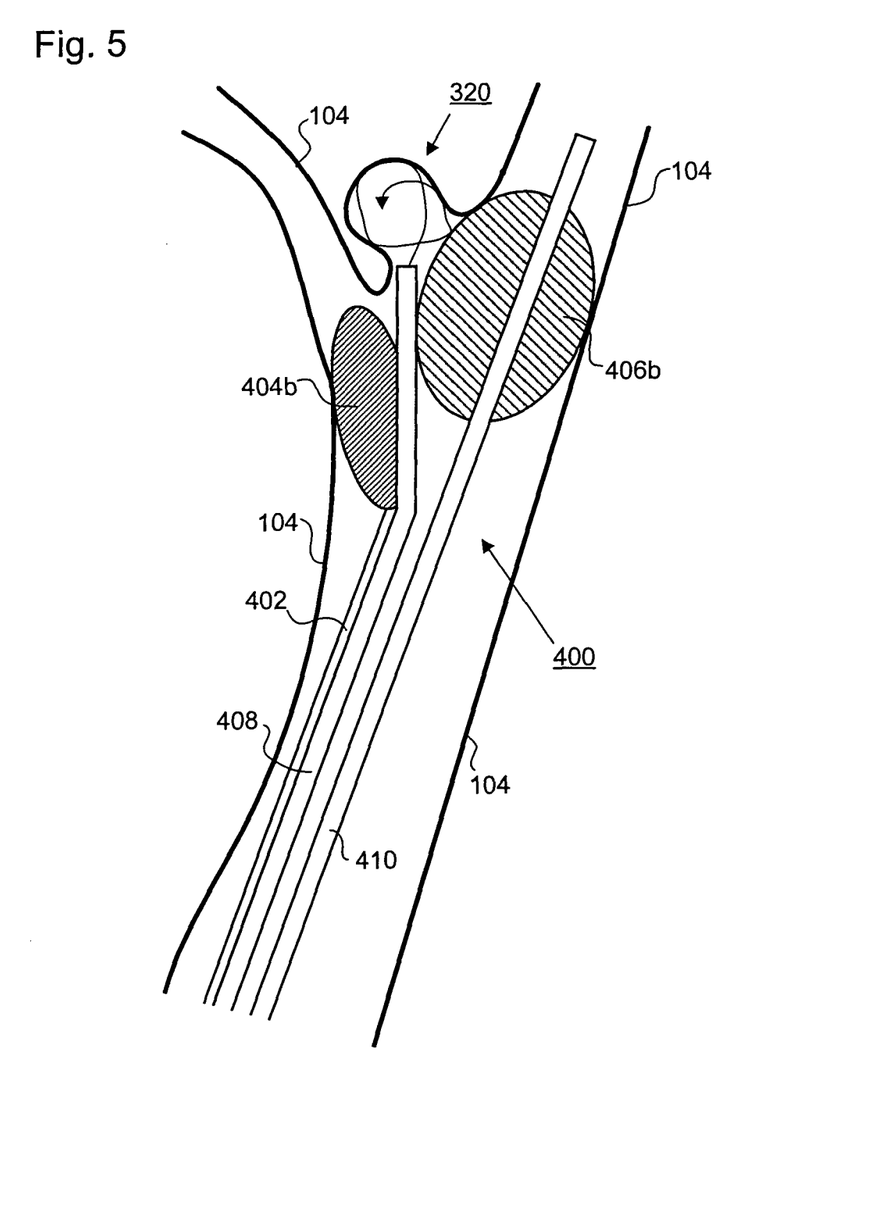
FIG. 5 illustrates an alternative deployment of the arrangement of FIG. 4d.

FIG. 5 shows an adaptation of the arrangement of FIG. 4d (i.e. the same apparatus deployed differently or a differently configured apparatus) in which the inflated first balloon 406b is used to deflect a deployment direction of occluding agent at a point in time after it has been output from the outlet 412. In this example, the inflated first balloon 406b is used to deflect occluding agent back into the aneurismal sac after it has been deflected by the inside of the aneurismal sac in a direction which, in the absence of the inflated first balloon 406b, might lead to escape of the occluding agent from the aneurismal sac. This arrangement reduces the risk of leakage of occluding agent into regions of the vessel 104 other than the aneurismal sac and helps to ensure efficient occlusion of the aneurismal sac.

The arrangement of FIG. 5 shows how deflection of the occluding agent can usefully be effected by the catheter of an embodiment after it has first been deflected by the inside of the aneurismal sac (or other interface within the body to be treated). However, alternatively or additionally, means may be provided to deflect the direction of deployment of the occluding agent immediately after it has left the outlet (before any deflection with other interfaces such as the interior of the aneurismal sac).

Figure 6:
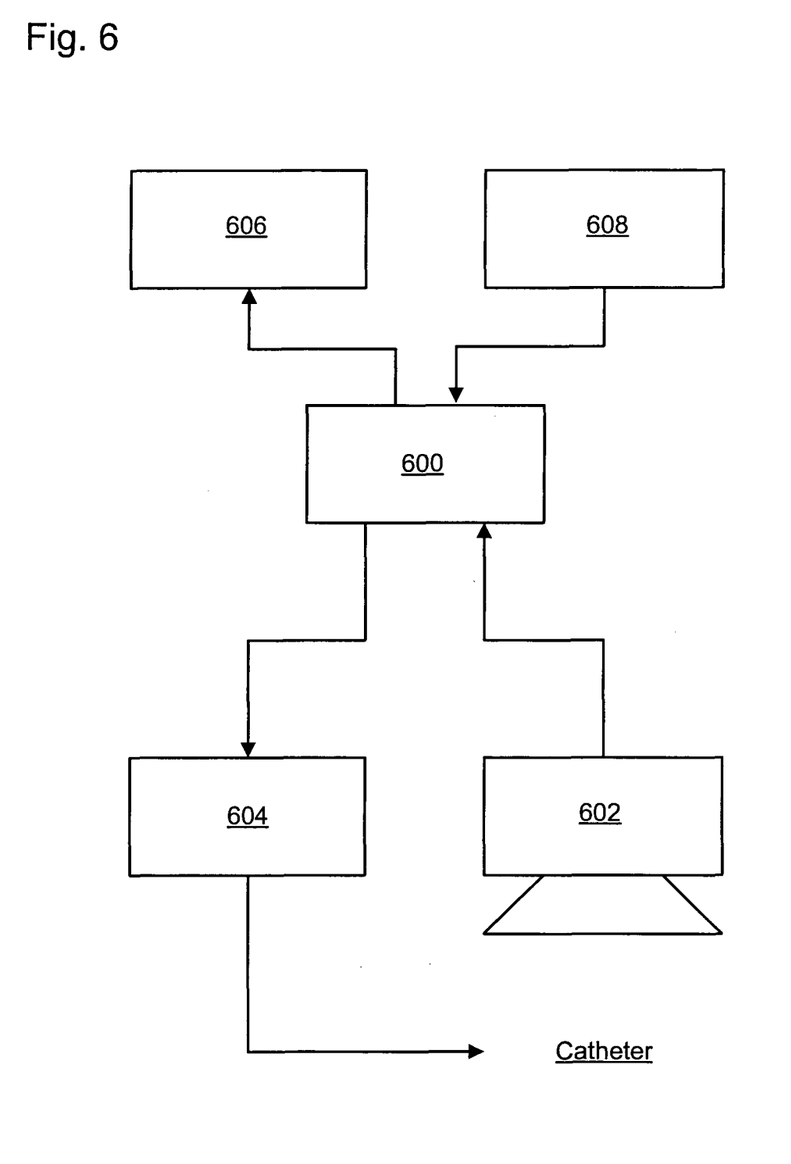
FIG. 6 shows a control system for assisting treatment of an aneurysm.

FIG. 6 is a schematic illustration of a control system for assisting treatment of aneurysms using a catheter 400 according to embodiments of the invention. A scanner 602 is provided for determining the position and/or orientation of an outlet 412 of a catheter 400 relative to an aneurysm to be treated and/or the direction of deployment of occluding agent entering the aneurismal sac. This information is fed as input to a controller 600, which may be implemented by a suitably programmed computer, for example. The controller 600 may process data input from the scanner 602 and present an image to a user via a display 606. Using the display 606 as reference, the user may then input directions via input means 608 (comprising a joystick or similar, for example) to direct the controller 600 to adjust the degree of actuation (e.g. degree of inflation) of first and/or second balloons 406a/406b/404a/404b in the catheter 400 in order to adjust the position and/or orientation of the outlet 412 relative to the aneurysm to be treated and/or the direction of deployment of occluding agent entering the aneurismal sac. This user input is processed by the controller 600 and suitable commands are issued to a balloon controller 604 configured to carry out the necessary adjustments to the degree of actuation of the balloons (e.g., by inflating or deflating the first and/or second balloons 406a/406b/404a/404b to the appropriate extent). The balloon controller 604 may comprise means for measuring a pressure within the first and/or second balloons 406a/406b/404a/404b, for example, or other means for determining a degree of actuation of the first and/or second balloons 406a/406b/404a/404b.

The invention claimed is:

1. A catheter for percutaneous treatment of an aneurysm, comprising:
   a first stem, a second stem, and a third stem;
   an outlet configured to deploy an occluding agent comprising a length of wire, wherein the second stem comprises the outlet;
   a first deflector for deflecting said occluding agent into said aneurysm, wherein the first stem comprises the first deflector;
   a second deflector, wherein the third stem comprises the second deflector; and
   the occluding agent;
   wherein said first and second deflectors are configured to be actuatable selectively and/or to a variable extent so as to cooperatively adjust the orientation of the second stem and thereby to adjust the at least one of the position and orientation of said outlet; and
   wherein said first deflector is configured to deflect said occluding agent back into said aneurysm after it has been deflected by the inside of said aneurysm.

2. The catheter according to claim 1, wherein said first deflector comprises a balloon configured to communicate with a source of fluid for inflating said balloon when said catheter is located in the region of said aneurysm.

3. The catheter according to claim 1, wherein said second deflector comprises a balloon configured to communicate with a source of fluid for inflating said balloon when said catheter is located in the region of said aneurysm.

4. The catheter according to claim 1, wherein said first and second deflectors are configured to be actuatable selectively and/or to a variable extent so as to cooperatively adjust the direction of deployment of said occluding agent.

5. The catheter according to claim 1, wherein said first deflector or said second deflector is configured to change a direction of deployment of a portion of occluding agent that has left the outlet relative to the direction of deployment that that portion of occluding agent had immediately prior to contact with the first deflector or the second deflector respectively.

6. The catheter according to claim 1, wherein said aneurysm is a cerebral aneurysm.

7. A method of treating an aneurysm, comprising:
   percutaneously inserting a catheter so that a distal end thereof is brought into the region of the aneurysm, the catheter comprising: a first stem, a second stem, a third stem, an outlet for deploying an occluding agent, a first deflector, and a second deflector, wherein the first stem comprises the first deflector, the second stem comprises the outlet, and the third stem comprises the second deflector, and wherein the first deflector and the second deflector are configured to be actuated to selectively and/or to a variable extent so as to cooperatively adjust the orientation of the second stem thereby to adjust at least one of the position and orientation of said outlet;
   actuating said first and second deflectors to cooperatively adjust the orientation of the second stem thereby to adjust at least one of the position and orientation of said outlet; and
   using said outlet to deploy an occluding agent, wherein said occluding agent comprises a length of wire; and
   using said first deflector to deflect said deployed occluding agent into said aneurysm; and
   arranging said first deflector so as to prevent escape of deployed occluding agent front an aneurysmal sac.

8. The method according to claim 7, wherein said wire is deployed by pushing said wire out of said outlet and said first deflector acts to promote formation of a coil of said wire inside said aneurysm.

9. The method according to claim 7, wherein said first deflector comprises a balloon, and said method further comprises inflating said balloon so as to deflect said occluding agent deployed from said outlet towards said aneurysm.

10. The method according to claim 7, further comprising selectively actuating said first and second deflectors so as to cooperatively adjust the direction of deployment of said occluding agent.

11. The method according to claim 7, wherein one or both of said first and second deflectors is/are actuatable to a plurality of different extents, and said method further comprises selectively actuating one or both of said first and second deflectors to a particular one of said plurality of different extents in order to cooperatively adjust the direction of deployment of said occluding agent.

12. The method according to claim 11, wherein the direction of adjustment of said occluding agent is adjusted at least partly by using at least one of the first and second deflectors to adjust at least one of the position and orientation of said outlet.

13. A catheter for percutaneous treatment of an aneurysm, comprising:
   a first stem, a second stem, and a third stem;
   an outlet configured to deploy an occluding agent comprising a length of wire, wherein the second stem comprises the outlet;
   a first deflector, wherein the first stem comprises the first deflector;
   a second deflector, wherein the third stem comprises the deflector; and
   the occluding agent;
   wherein said first and second deflectors are configured to be actuatable selectively and/or to a variable extent so as cooperatively to adjust the orientation of the second stem thereby to adjust the position and/or orientation of said outlet.

* * * * *

UNITED STATES PATENT AND TRADEMARK OFFICE
CERTIFICATE OF CORRECTION

PATENT NO.       : 9,277,923 B2
APPLICATION NO.  : 13/262341
DATED            : March 8, 2016
INVENTOR(S)      : Permjit Rangi It is certified that error appears in the above-identified patent and that said Letters Patent is hereby corrected as shown below:

Title Page

Item (73), Assignee:

Delete "HOSPITALS NHS TRUST" and replace with --UNIVERSITY HOSPITALS NATIONAL HEALTH SERVICE TRUST--.

Signed and Sealed this
Twenty-first Day of June, 2016

Michelle K. Lee
*Director of the United States Patent and Trademark Office*